(12) United States Patent
Kinsho et al.

(10) Patent No.: US 9,708,241 B2
(45) Date of Patent: Jul. 18, 2017

(54) METHODS FOR PRODUCING β-CYCLOLAVANDULAL AND DERIVATIVE OF SAME

(71) Applicant: SHIN-ETSU CHEMICAL CO., LTD., Tokyo (JP)

(72) Inventors: Takeshi Kinsho, Joetsu (JP); Naoki Ishibashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/021,168

(22) PCT Filed: Sep. 11, 2014

(86) PCT No.: PCT/JP2014/074082
§ 371 (c)(1),
(2) Date: Mar. 10, 2016

(87) PCT Pub. No.: WO2015/037665
PCT Pub. Date: Mar. 19, 2015

(65) Prior Publication Data
US 2016/0221924 A1    Aug. 4, 2016

(30) Foreign Application Priority Data

Sep. 12, 2013  (JP) .................... 2013-189555

(51) Int. Cl.
| C07C 69/00 | (2006.01) |
| C07C 67/40 | (2006.01) |
| C07C 29/14 | (2006.01) |
| C07C 67/14 | (2006.01) |
| C07C 45/42 | (2006.01) |
| C07C 41/01 | (2006.01) |

(52) U.S. Cl.
CPC .............. C07C 67/40 (2013.01); C07C 29/14 (2013.01); C07C 41/01 (2013.01); C07C 45/42 (2013.01); C07C 67/14 (2013.01); *C07C 2101/16* (2013.01)

(58) Field of Classification Search
None
See application file for complete search history.

(56) References Cited

U.S. PATENT DOCUMENTS

2002/0161051 A1   10/2002  Chow et al.
2005/0131004 A1   6/2005   Mentzel et al.

FOREIGN PATENT DOCUMENTS

CN     101323563 A    12/2008
JP     57-134428      8/1982

(Continued)

OTHER PUBLICATIONS

Mimoun et al. J. Org. Chem. 1999, 64, 2582-2589.*

(Continued)

*Primary Examiner* — Yong Chu
*Assistant Examiner* — Ana Z Muresan
(74) *Attorney, Agent, or Firm* — Myers Bigel, P.A.

(57) ABSTRACT

Target compounds are synthesized simply, efficiently and selectively. More specifically, provided are a method for producing (2,4,4-trimethyl-1-cyclohexene)carbaldehyde, comprising the steps of: reacting the carbonyl group of 2,4,4-trimethyl-2-cyclohexenone (1) to obtain a 2,4,4-trimethyl-2-cyclohexenylidenemethyl ether compound (2) and hydrolyzing Compound (2) to obtain the (2,4,4-trimethyl-1-cyclohexene)carbaldehyde (3); a method for producing (2,4,4-trimethyl-1-cyclohexene)methanol, comprising a step of reducing Compound (3) to obtain the (2,4,4-trimethyl-1-cyclohexene)methanol (4); and a method for producing a (2,4,4-trimethyl-1-cyclohexenyl)methyl ester compound, comprising a step of esterifying Compound (4) to obtain the (2,4,4-trimethyl-1-cyclohexenyl)methyl ester compound (5).

3 Claims, No Drawings

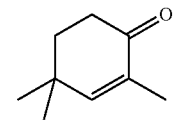 (1)

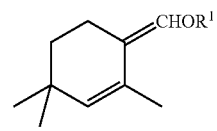

(2)

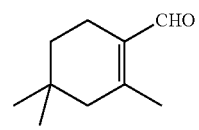

(3)

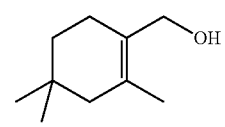

(4)

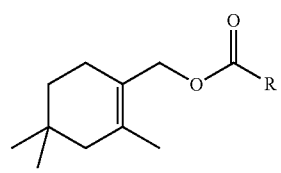

(5)

(56) References Cited

FOREIGN PATENT DOCUMENTS

| JP | 62-051636 | 3/1987 |
|---|---|---|
| JP | 10-251165 | 9/1998 |
| JP | 2004-524312 A | 8/2004 |
| JP | 2007-513922 A | 5/2007 |
| JP | 2009-500409 A | 1/2009 |
| WO | WO 02/068384 A2 | 9/2002 |
| WO | WO 2007/005177 A1 | 1/2007 |

OTHER PUBLICATIONS

Machine translation for CN101323563.*
Eilbracht et al. "Regioselektivität und sterischer Verlauf der Lewis-Säure-induzierten Ringerweiterung von Cyclohexadien-Komplexen mit Kohlenmonoxid", *Chem. Ber.* 117:3473-3489 (1984).
Gandhi et al. "The Synthesis of β- Cyclolavandulal", *Science and Culture* 24(6):292-293 (1958).
Jikken Kagaku Koza 20 Yuki Gosei II *Alcohol Amine* $4^{th}$ *edition* pp. 1-10 (1992).
Jikken Kagaku Koza 22 Yuki Gosei IV *San Amino-san Peptide*, $4^{th}$ *edition* pp. 50-51 (1992).
Jikken Kagaku Koza 20 Yuki Gosei II *Alcohol, Amine 1 4 2 Hydroboration*, $4^{th}$ *edition* pp. 72-81.
Kinoshita et al. "Concise Construction of N-Alkylated Phenazinone Skeletons: Synthesis of Lavanducyanin (WS-9659A)", *Synlett* pp. 186-188 (1995).
Nakayama et al. "WS-9659 A and B, Novel Testosterone 5α-Reductase Inhibitors Isolated from a *Streptomyces*", *The Journal of Antibiotics* 42:1230-1234 (1989).
Oda et al. "An efficient synthetic method for β-cyclolavandulal and its corresponding alcohol", *Recl. Trav. Chim. Pays-Bas* 115:438-440 (1996).
Rao et al. "Secondary metabolites and biological studies of seeds of *Carum carvi* Linn.", *J. Pharmacy Research* 4(7):2126-2128 (2011).
Sugie et al. "Identification of a sex pheromone component of the Japanese mealybug, *Planococcus kraunhiae* (Kuwana)", *Appl. Entomol. Zool.* 43(3):369-375 (2008).
Tabata et al. "Cyclolavandulyl butyrate: an attractant for a mealybug parasitoid, *Anagyrus sawadai* (Hymenoptera: Encyrtidae)", *Appl. Entomol. Zool.* 46:117-123 (2011).
Vellutini et al. "β-Cyclolavandulyl and β-isocyclolavandulyl esters from *Peucedanum paniculatum* L., an endemic species to Corsica", *Phytochemistry* 66:1956-1962 (2005).
International Search Report corresponding to International Application No. PCT/JP2014/074081 mailed Dec. 16, 2014.
International Preliminary Report on Patentability corresponding to International Application No. PCT/JP2014/074081 issued Mar. 15, 2016.
International Search Report corresponding to International Application No. PCT/JP2014/074082 mailed Dec. 9, 2014.
International Preliminary Report on Patentability corresponding to International Application No. PCT/JP2014/074082 issued Mar. 15, 2016.
Bourquin et al. "Die Cyclisation des Lavandulols" *Helvetica Chimica Acta* 32:1564-1568 (1949).
Office Action corresponding to Chinese Patent Application No. 201480049929.1 (12 pages) (dated Dec. 19, 2016).
Office Action corresponding to Japanese Patent Application No. 2014-185272 (4 pages) (dated May 29, 2017).

* cited by examiner

METHODS FOR PRODUCING β-CYCLOLAVANDULAL AND DERIVATIVE OF SAME

RELATED APPLICATIONS

This application is a 35 U.S.C. §371 national phase application of PCT Application PCT/JP2014/074082 filed Sep. 11, 2014, which claims priority to Japanese Application No. 2013-189555 filed Sep. 12, 2013. The entire contents of each are incorporated herein by reference in its entirety.

TECHNICAL FIELD

The present invention relates to methods for producing a monoterpene aldehyde, an alcohol and derivatives thereof that are important as biologically active substances or synthetic intermediates thereof. More specifically, the present invention relates to methods for producing (2,4,4-trimethyl-1-cyclohexene)carbaldehyde known as a general name of β-cyclolavandulal, (2,4,4-trimethyl-1-cyclohexene)methanol known as a general name of β-cyclolavandulol, and a (2,4,4-trimethyl-1-cyclohexenyl)methyl ester compound derived from the alcohol compound.

BACKGROUND ART (2,4,4-trimethyl-1-cyclohexene)carbaldehyde (β-cyclolavandulal) has been isolated from caraway, *Carum carvi* Linn., grown in India and used as a folk medicine and from fungi as a secondary metabolite (Non-Patent Document 1).

The (2,4,4-trimethyl-1-cyclohexene)carbaldehyde (β-cyclolavandulal) is also known as a constituent of WS-9659A (lavanducyanine) and WS-9659B, which have been isolated from actinomycete *Streptomyces* as inhibitors of testosterone 5α-reductase (Non-Patent Document 2).

Vellutini et al. have isolated a total of eight compounds including (2,4,4-trimethyl-1-cyclohexenyl)methyl esters (general name: β-cyclolavandulyl esters) and 4,4,6-trimethyl-1-cyclohexenyl)methyl esters (general name: β-isocyclolavandulyl esters) from essential oils of leaves and roots of *Peucedanum paniculatum* Linn. grown in Corsica, and determined the structures thereof (Non-Patent Document 3).

Oda et al. have reported the syntheses of (2,4,4-trimethyl-1-cyclohexene)carbaldehyde (general name: β-cyclolavandulal) and (2,4,4-trimethyl-1-cyclohexene)methanol (general name: β-cyclolavandulol) from 3,3-dimethylcyclohexanone as a starting material. In the syntheses, 3,3-dimethylcyclohexanone was subjected to methoxycarbonylation to obtain a ketoester; the ketoester was converted into an enol phosphate derivative; then a methyl group was introduced thereto with dimethyllithium cuprate; the resulting product was reduced with lithium aluminum hydride to obtain the (2,4,4-trimethyl-1-cyclohexene)methanol; and the (2,4,4-trimethyl-1-cyclohexene)methanol was oxidized with pyridinium chlorochromate (PCC) to obtain (2,4,4-trimethyl-1-cyclohexene)carbaldehyde (Non-Patent Document 4).

Kinoshita et al. have reported the synthesis of (2,4,4-trimethyl-1-cyclohexene)methanol as a synthetic intermediate of WS-9659A (lavanducyanine) by using 3,3-dimethylglutaric anhydride as a starting material in an overall yield of 33%. The synthesis includes five steps of reduction into a lactone, conversion with methyllithium into a methyl hemiacetal, conversion with iodine into a keto iodide, alkylation and condensation with trimethyl phosphonoacetate, and reduction with diisobutylaluminum into the allyl alcohol (Non-Patent Document 5).

Gandhi et al. have reported the synthesis of (2,4,4-trimethyl-1-cyclohexene)carbaldehyde (Non-Patent Document 6). According to the abstract, 3,3-dimethylcyclohexanone as a raw material was reached with ethyl formate for condensation to obtain 3,3-dimethyl-6-(hydroxymethylene)cyclohexanone, and then the 3,3-dimethyl-6-(hydroxymethylene)cyclohexanone was reacted with isobutyl alcohol under an acidic condition to obtain a corresponding isobutoxymethylene derivative in a yield of 61%. The isobutoxymethylene derivative further was treated with methylmagnesium iodide, and hydrolyzed with dilute sulfuric acid to obtain the target compound in a yield of 66%.

(2,4,4-Trimethyl-2-cyclohexenyl)methyl butyrate ester [another name: (2,4,4-trimethyl-2-cyclohexenyl)methyl n-butyrate, cyclolavandulyl butyrate] has been isolated as an attractant of an important parasitic wasp in controlling mealybugs. More specifically, Tabata et al. have found (2,4,4-trimethyl-2-cyclohexenyl)methyl butyrate ester, which is a substance attracting *Anagyrus sawadai* that is one of the wasps living parasitically with the mealybug, from by-products generated when lavandulol is treated with butyryl chloride to synthesize lavandulyl butyrate, have isolated the active substance, and have determined the structure thereof (Non-Patent Document 7). The lavandulol as the starting material was treated with butyryl chloride to obtain (2,4,4-trimethyl-2-cyclohexenyl)methyl butyrate ester in a yield of 1.2%. (2,4,4-Trimethyl-1-cyclohexenyl)methyl butyrate ester, which is a regioisomer of the (2,4,4-trimethyl-2-cyclohexenyl)methyl butyrate ester with respect to the position of a double bond, is similar to 2-isopropylidene-5-methyl-4-hexen-1-yl butyrate ester (fujikonyl butyrate, Non-Patent Document 8), which is known as a sex pheromone of *Planococcus kraunhiae*, with respect to the position of a double bond from a polar group and has attracted attention due to attractive activities to parasitic wasps.

NON-PATENT DOCUMENTS

Non-Patent Document 1: Journal of Pharmacy Research, 4, 2126-2128 (2011)
Non-Patent Document 2: Journal of Antibiotics, 42, 1230-1234 (1989)
Non-Patent Document 3: Phytochemistry, 66, 1956-1962 (2005)
Non-Patent Document 4: Red. Tray. Chim. Pays-Bas, 115, 438-440 (1996)
Non-Patent Document 5: Synlett, 186-188 (1995)
Non-Patent Document 6: Science and Culture, 24, 292 (1958)
Non-Patent Document 7: Appl. Entomol. Zool., 46, 117-123 (2011)
Non-Patent Document 8: Appl. Entomol. Zool., 43, 369-375 (2008)

SUMMARY OF THE INVENTION

Problems to be Solved by the Invention

However, these synthesis examples involve a long process to obtain a low yield or involve purification of an intermediate which is difficult to perform on an industrial scale, such as purification with chromatography. Thus, it is considered to be very difficult to supply a product in a required amount.

In view of the above circumstances, an object of the present invention is to provide a simple, efficient and selective production method in order to supply a sufficient amount of product required for biological, pharmacological or agronomical activity studies, practical applications and other purposes.

Means for Solving the Problems

As a result of intensive studies for achieving the object, the inventors of the present invention have found that production of (2,4,4-trimethyl-1-cyclohexene)carbaldehyde and (2,4,4-trimethyl-1-cyclohexene)methanol from 2,4,4-trimethyl-2-cyclohexenone as a starting material and further production of a (2,4,4-trimethyl-1-cyclohexenyl)methyl ester compound through esterification of the (2,4,4-trimethyl-1-cyclohexene)methanol can be carried out in high yields with high selectivity on an industrial scale, and have accomplished the present invention.

In an aspect of the present invention, there is provided a method for producing (2,4,4-trimethyl-1-cyclohexene)carbaldehyde, comprising the steps of: reacting a carbonyl group of 2,4,4-trimethyl-2-cyclohexenone represented by Formula (1) below to obtain a 2,4,4-trimethyl-2-cyclohexenylidenemethyl ether compound represented by General Formula (2) below; and hydrolyzing the 2,4,4-trimethyl-2-cyclohexenylidenemethyl ether to obtain the (2,4,4-trimethyl-1-cyclohexene)carbaldehyde represented by Formula (3) below.

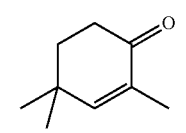

(1)

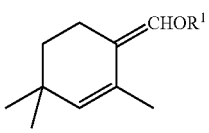

(2)

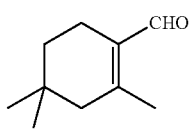

(3)

wherein $R^1$ represents a monovalent hydrocarbon group having 1 to 8 carbon atoms.

In another aspect of the present invention, there is provided a method for producing (2,4,4-trimethyl-1-cyclohexene)methanol, comprising the steps comprised by the above method to obtain the (2,4,4-trimethyl-1-cyclohexene)carbaldehyde; and a step of reducing the (2,4,4-trimethyl-1-cyclohexene)carbaldehyde to obtain the (2,4,4-trimethyl-1-cyclohexene)methanol represented by Formula (4):

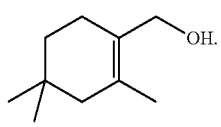

(4)

In still another aspect of the present invention, there is provided a method for producing a (2,4,4-trimethyl-1-cyclohexenyl)methyl ester compound, comprising the steps comprised by the above method to obtain the (2,4,4-trimethyl-1-cyclohexene)methanol; and a step of esterifying the (2,4,4-trimethyl-1-cyclohexene)methanol to obtain the (2,4,4-trimethyl-1-cyclohexenyl)methyl ester compound represented by General Formula (5):

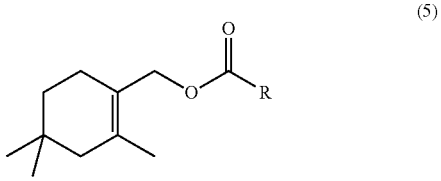

(5)

wherein R represents a hydrogen atom or a monovalent hydrocarbon group having 1 to 10 carbon atoms.

Effect of the Invention

According to the present invention, a monoterpene alcohol and a derivative thereof which are important as biologically active substances or synthetic intermediates thereof, that is, (2,4,4-trimethyl-1-cyclohexene)carbaldehyde (3), (2,4,4-trimethyl-1-cyclohexene)methanol (4), and a (2,4,4-trimethyl-1-cyclohexenyemethyl ester compound (5) can be synthesized simply, efficiently and selectively.

DETAILED DESCRIPTION

Embodiments of the present invention will now be described in detail, but the present invention is not limited to them.

According to the present invention, starting material 2,4,4-trimethyl-2-cyclohexenone (1) can be easily synthesized, for example, from an aldehyde derivative enamine and ethyl vinyl ketone by the enamine method (G. Stork et al., Journal of Organic Chemistry, 85, 207-221; and Y. Chan et al., Organic Syntheses, Coll. Vol. 6, 496-498). Subsequent one-carbon (C1) homologation and functional group transformation of the starting material can produce respective target compounds.

The first step is a step of converting the carbonyl group of 2,4,4-trimethyl-2-cyclohexenone (1) into an alkoxymethylene group to obtain a 2,4,4-trimethyl-2-cyclohexenylidenemethyl ether compound (2).

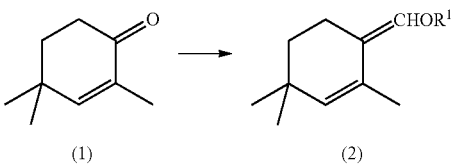

$R^1$ is a monovalent hydrocarbon group having 1 to 8 carbon atoms and preferably includes primary alkyl groups having 1 to 8 carbon atoms such as a methyl group, an ethyl group, an n-propyl group and an isobutyl group; and a benzyl group. $R^1$ is particularly preferably a methyl group or an ethyl group.

In this step, one of various known methods can be used and the Wittig reaction is preferred. More specifically, in a preferable example, a phosphorus ylide reagent prepared by treating a triphenylalkoxymethylphosphonium halide with a base in a solvent is a triphenylphosphonium alkoxymethylide [(C$_6$H$_5$)$_3$P═CHOR$^1$] wherein R$^1$ is the same as the above, and is reacted with 2,4,4-trimethyl-2-cyclohexenone (1).

Examples of the starting material triphenylalkoxymethylphosphonium halide in the preparation of the phosphorus ylide reagent include triphenylalkoxymethylphosphonium chlorides, triphenylalkoxymethylphosphonium bromides, and triphenylalkoxymethylphosphonium iodides.

Examples of the solvent in the preparation of the phosphorus ylide reagent include ethers such as diethyl ether, di-n-butyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and propionitrile. The solvent can be used singly or in combination of two or more.

Examples of the base in the preparation of the phosphorus ylide reagent include organometallic reagents such as methyllithium, ethyllithium, n-butyllithium and methylmagnesium chloride; alkoxides such as sodium methoxide, sodium ethoxide and potassium t-butoxide; metal amides such as lithium diisopropylamide, lithium hexamethyldisilazide, sodium hexamethyldisilazide and lithium dicyclohexylamide; metal hydrides such as sodium hydride, potassium hydride and calcium hydride; and dimsyl sodium. The amount of the base is preferably 0.5 to 2 mol, more preferably 1.0 to 1.5 mol relative to 1 mol of the triphenylalkoxymethylphosphonium halide.

The reaction temperature in the preparation of the phosphorus ylide reagent is preferably −78 to 50° C., more preferably −78° C. to room temperature (5 to 35° C., the same applies hereinafter), even more preferably −10° C. to room temperature.

The reaction time in the preparation of the phosphorus ylide reagent is preferably 5 minutes to 18 hours. It is more preferably 5 minutes to 1 hour from the standpoint of reagent stability.

The triphenylphosphonium alkoxymethylide prepared in this manner, which is the phosphorus ylide reagent, is reacted with the ketone 2,4,4-trimethyl-2-cyclohexenone (1). Typically, the ketone without a solvent or the ketone diluted with a solvent is added dropwise to a solution of the phosphorus ylide reagent.

The solvent to be used for the dilution may include the same examples as those of the solvent used in the preparation of the phosphorus ylide reagent.

The reaction temperature during the Wittig reaction is preferably −78 to 50° C., more preferably −78° C. to room temperature, even more preferably −10° C. to room temperature.

The amount of the phosphorus ylide reagent to be used for the Wittig reaction is preferably 0.5 to 50 mol, more preferably 1.0 to 10 mol relative to 1 mol of the ketone as the reactant. It is even more preferably 1.0 to 2.5 mol relative to 1 mol of the ketone from the standpoint of yield and cost efficiency.

The reaction time of the Wittig reaction is preferably the time sufficient to complete the reaction, which may be determined by monitoring the progress of the reaction through gas chromatography (GC) or thin-layer chromatography (TLC) and is typically 30 minutes to 96 hours.

The posttreatment of the Wittig reaction, which is the isolation and purification of the target compound, can be carried out by a method appropriately selected from purification methods commonly used in organic syntheses, such as vacuum distillation and various types of chromatography. The vacuum distillation is preferable from the standpoint of industrial cost efficiency. In this case, triphenylphosphine oxide generated by the reaction can be precipitated with a poor solvent and removed by filtration or the like by advance. Alternatively, the reaction mixture can be directly distilled under reduced pressure without removal of triphenylphosphine oxide. As explained above, the 2,4,4-trimethyl-2-cyclohexenylidenemethyl ether compound (2) is obtained. When the target compound has sufficient purity, the product without purification can be directly used in the subsequent step.

The next step is a step of converting the 2,4,4-trimethyl-2-cyclohexenylidenemethyl ether compound (2) into (2,4,4-trimethyl-1-cyclohexene)carbaldehyde (3).

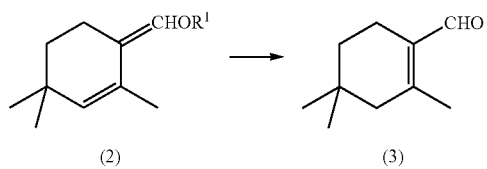

The inventors have found that the 2,4,4-trimethyl-2-cyclohexenylidenemethyl ether compound (2), which is an enol ether compound, is hydrolyzed under an acidic condition to produce not (2,4,4-trimethyl-2-cyclohexene)carbaldehyde, but isomer (2,4,4-trimethyl-1-cyclohexene)carbaldehyde as a substantially single product. The former is a β,γ-unsaturated aldehyde having a double bond at the β-position of the carbonyl group and is considered to be a direct product of the hydrolysis, while the latter is an α,β-unsaturated aldehyde having a double bond at the α-position of the carbonyl group. The ratio of α,β-isomer to β,γ-isomer is found to be greater than 99:1. Thus, this step is suitable for producing (2,4,4-trimethyl-1-cyclohexene)carbaldehyde (3).

The hydrolysis reaction is carried out in the presence of water typically in an acidic condition. An additional solvent can be used other than the water.

Examples of the acid include inorganic acids such as hydrochloric acid, hydrobromic acid, sulfuric acid and nitric acid; and organic acids such as oxalic acid, trifluoroacetic acid, methanesulfonic acid, benzenesulfonic acid and p-toluenesulfonic acid. The acid is used singly or in combination of two or more. The hydrochloric acid is particularly preferred from the standpoint of availability at low cost in large amounts on an industrial scale.

The amount of the acid depends on the type of R$^1$ and is preferably in a range of 0.001 to 500 mol, more preferably 0.01 to 100 mol relative to 1 mol of the ether compound.

The additional solvent can be selected from, for example, chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran, 1,4-dioxane, ethylene glycol dimethyl ether and diethylene glycol dimethyl ether; alcohols such as methanol, ethanol, 1-propanol, 2-propanol, ethylene glycol monomethyl ether and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The additional solvent can be used singly or in combination of two or more.

The reaction temperature of the hydrolysis reaction can be selected appropriately in consideration of the type of an acid or solvent to be used and reaction conditions. It is in general preferably −20° C. to the boiling point of a solvent, more preferably −20° C. to room temperature (5 to 35° C., the same applies hereinafter).

The isolation and purification method of the target compound (2,4,4-trimethyl-1-cyclohexene)carbaldehyde (3) can be appropriately selected from purification methods commonly used in organic syntheses, such as vacuum distillation and various types of chromatography. The vacuum distillation is preferable from the standpoint of industrial cost efficiency.

As explained above, (2,4,4-trimethyl-1-cyclohexene)carbaldehyde (3) can be obtained from 2,4,4-trimethyl-2-cyclohexenone (1) in a high yield with high selectivity.

The next step is a step of reducing the carbonyl group of the (2,4,4-trimethyl-1-cyclohexene)carbaldehyde (3) obtained by the above method into a hydroxy group to obtain (2,4,4-trimethyl-1-cyclohexene)methanol (4).

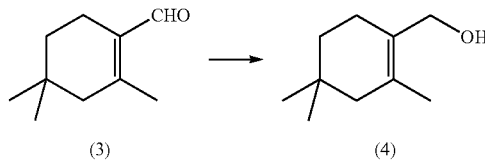

As the reduction reaction, a known conversion reaction from an aldehyde to an alcohol can be employed. In the reduction reaction, the reactant (2,4,4-trimethyl-1-cyclohexene)carbaldehyde (3) is reacted with a reducing agent, typically in a solvent, with optional cooling or heating.

Examples of the reducing agent may include hydrogen; boron compounds such as borane, alkylboranes, dialkylboranes and bis(3-methyl-2-butyl)borane; dialkylsilanes; trialkylsilanes; alkylaluminums; dialkylaluminums; metal hydrides such as sodium hydride, lithium hydride, potassium hydride and calcium hydride; complex hydrides such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy)aluminum hydride, lithium triethylborohydride and diisobutylaluminum hydride; and alkoxy or alkyl derivatives thereof. The complex hydrides are preferably used from the standpoint of reaction conditions, ease in posttreatment and product isolation, and others.

The amount of the reducing agent varies depending on a type of reducing agent to be used, reaction conditions and others. It is in general preferably 0.5 mol or more, more preferably 0.9 to 8.0 mol relative to 1 mol of (2,4,4-trimethyl-1-cyclohexene)carbaldehyde (3).

Examples of the solvent to be used in the reduction reaction include water; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; alcohols such as methanol, ethanol, 1-propanol, 2-propanol, ethylene glycol monomethyl ether and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The solvent can be used singly or in combination of two or more.

The solvent to be used in the reduction reaction is appropriately selected in accordance with the type of the reducing agent to be used. As for the preferred combination of the reducing agent and the solvent, when sodium borohydride is used as the reducing agent, the solvent is selected, for example, from water, a mixed solvent of water and ether, a mixed solvent of water and hydrocarbon, and a mixed solvent of water and alcohol. When lithium borohydride is used as the reducing agent, the solvent is selected, for example, from ether, a mixed solvent of ether and alcohol, and a mixed solvent of ether and hydrocarbon. When lithium aluminum hydride is used as the reducing agent, the solvent is selected, for example, from ether, and a mixed solvent of ether and hydrocarbon.

The reaction temperature or the reaction time of the reduction reaction varies depending on a reagent and a solvent to be used. For example, when lithium aluminum hydride in tetrahydrofuran is used as the reducing agent, the reaction temperature is preferably −78 to 50° C., more preferably −70 to 20° C.

The reaction time of the reduction reaction may be preferably the time sufficient to complete the reaction, which may be determined by monitoring the progress of the reaction through gas chromatography (GC) or silica gel thin-layer chromatography (TLC), from the standpoint of yield. It is typically 0.5 to 96 hours.

The isolation and purification method of the target compound (2,4,4-trimethyl-1-cyclohexene)methanol (4) can be appropriately selected from purification methods commonly used in organic syntheses, such as vacuum distillation and various types of chromatography. The vacuum distillation is preferable from the standpoint of industrial cost efficiency. As explained above, (2,4,4-trimethyl-1-cyclohexene)methanol (4) can be obtained from 2,4,4-trimethyl-2-cyclohexenone (1) in a high yield with high selectivity.

The obtained (2,4,4-trimethyl-1-cyclohexene)methanol (4) can be esterified into a (2,4,4-trimethyl-1-cyclohexenyl) methyl ester compound (5).

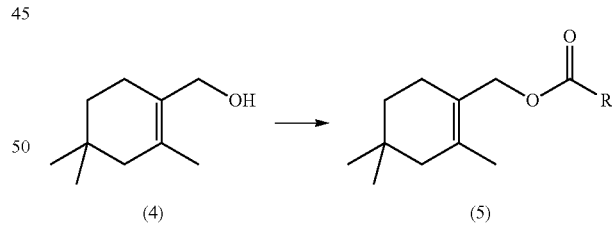

R represents a hydrogen atom or a monovalent hydrocarbon group having 1 to 10 carbon atoms, preferably 1 to 5 carbon atoms. Depending on the type of R, the ester compound can have various structures. For example, when R is a hydrogen atom, the ester compound is a formate.

Specific examples of the monovalent hydrocarbon group of R include linear, branched or cyclic saturated monovalent hydrocarbon groups such as a methyl group (an acetate as the ester compound), an ethyl group (a propionate as the ester compound), an n-propyl group, an isopropyl group, an n-butyl group, an isobutyl group, a sec-butyl group, a tert-butyl group, an n-pentyl group, an isopentyl group, an n-hexyl group, an n-octyl group, an n-nonyl group, an n-decyl group, a cyclopropyl group, a cyclobutyl group, a cyclopentyl group, a cyclohexyl group, a methylcyclopropyl group, dimethylcyclopropyl groups (including all regioisomers with respect to the positions of methyl groups, the same applies hereinafter), methylcyclobutyl groups, dimethylcyclobutyl groups, trimethylcyclobutyl groups, tetramethylcyclobutyl groups, methylcyclopentyl groups, dimethylcyclopentyl groups, trimethylcyclopentyl groups, tetramethylcyclopentyl groups, methylcyclohexyl groups, dimethylcyclohexyl groups and trimethylcyclohexyl groups; linear, branched or cyclic unsaturated monovalent hydrocarbon groups such as a vinyl group (an acrylate as the ester compound), a 1-propenyl group (a crotonate as the ester compound), a 2-propenyl group (a methacrylate as the ester compound), a 2-methyl-1-propenyl group (a senecioate as the ester compound), an ethynyl group (a propiolate as the ester compound), a propynyl group, a 1-butyny group, cyclopentenyl groups (including all regioisomers with respect to the position of a double bond, the same applies hereinafter), cyclohexenyl groups, dicyclohexadienyl groups and methylcyclohexenyl groups; and hydrocarbon groups that are isomeric with these groups.

For the esterification reaction, a known ester production method including a reaction with an acylating agent, a reaction with a carboxylic acid, and a transesterification can be employed.

When the reaction with an acylating agent is selected as the esterification reaction, the solvent can be selected preferably from chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The solvent can be used singly or in combination of two or more.

The acylating agent is preferably an acid halide or an acid anhydride including mixed acid anhydrides. Examples of the acid halide preferably include acid chlorides (RCOCl wherein R corresponds to a monovalent hydrocarbon group of R in Formula (5)) and acid bromides (RCOBr wherein R corresponds to R in Formula (5)). Examples of the acid anhydride including mixed acid anhydrides preferably include RCOOX wherein R corresponds to R in Formula (5) wherein X represents a leaving group such as $R^2C=O$ wherein $R^2$ represents a hydrogen atom or a monovalent hydrocarbon group having 1 to 10 carbon atoms, preferably 1 to 5 carbon atoms, may be the same as or different from R, preferably the same as R, and includes the same examples as those for R. Examples of leaving group X further include a trifluoroacetyl group, a methanesulfonyl group, a trifluoromethanesulfonyl group, a benzenesulfonyl group, a p-toluenesulfonyl group, and a p-nitrophenyl group.

In the reaction with the acylating agent, the reactant (2,4,4-trimethyl-2-cyclohexene)methanol (4), the acylating agent and a base such as triethylamine, diisopropylethylamine, N,N-dimethylaniline, pyridine and 4-dimethylaminopyridine are sequentially or simultaneously added in the solvent and reacted. In the reaction with an acylating agent such as an acid anhydride, the reaction can be carried out in the presence of an acid catalyst selected from inorganic acids such as hydrochloric acid, hydrobromic acid, sulfuric acid and nitric acid; and organic acids such as oxalic acid, trifluoroacetic acid, methanesulfonic acid, benzenesulfonic acid and p-toluenesulfonic acid, instead of the base.

The amount of the acylating agent depends on the structure of the reactant and is preferably in a range of 1 to 40 mol, more preferably 1 to 5 mol relative to 1 mol of the reactant alcohol compound.

The reaction temperature of the acylation reaction can be selected appropriately in accordance with the type of an acylating agent to be used and reaction conditions. It is in general preferably −50° C. to the boiling point of a solvent, more preferably −20° C. to room temperature.

When the reaction with a carboxylic acid is carried out as the esterification, the reaction is a dehydration reaction of the carboxylic acid and the reactant alcohol compound (2,4,4-trimethyl-2-cyclohexene)methanol (4), typically in the presence of an acid catalyst.

The amount of the carboxylic acid depends on the structure of the reactant and is preferably in a range of 1 to 40 mol, more preferably 1 to 5 mol relative to 1 mol of the reactant alcohol.

Examples of the acid catalyst to be used for the reaction with a carboxylic acid include inorganic acids such as hydrochloric acid, hydrobromic acid, sulfuric acid and nitric acid; and organic acids such as oxalic acid, trifluoroacetic acid, methanesulfonic acid, benzenesulfonic acid and p-toluenesulfonic acid. The acid catalyst is used singly or in combination of two or more. The amount of the acid catalyst is preferably 0.001 to 1 mol, more preferably a catalytic amount of 0.01 to 0.05 mol relative to 1 mol of the reactant alcohol compound.

The solvent to be used for the reaction with a carboxylic acid can include the same examples as those of the solvent used in the reaction with an acylating agent. The reaction temperature is in general preferably −50° C. to the boiling point of a solvent. The reaction may be carried out while removing generated water from the system by azeotropy, making use of a solvent including hydrocarbons such as hexane, heptane, benzene, toluene, xylene and cumene. In this case, the water can be distilled off while the reaction mixture is refluxed at the boiling point of a solvent at normal pressure. Alternatively, the water can be distilled off at a temperature lower than the boiling point under reduced pressure.

When the transesterification is carried out as the esterification, the reactant alcohol compound is reacted with a carboxylic ester compound produced from a corresponding carboxylic acid and a lower alcohol in the presence of a catalyst, while removing the resulting lower alcohol.

The carboxylic ester compound is preferably a primary alkyl ester and is particularly preferably a methyl ester, an ethyl ester or an n-propyl ester from the standpoint of price and ease in progress of the reaction. The amount of the carboxylate ester compound depends on the structure of the reactant and is preferably in a range of 1 to 40 mol, more preferably 1 to 5 mol relative to 1 mol of the reactant alcohol compound.

Examples of the catalyst to be used for the transesterification include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; bases such as sodium methoxide, sodium ethoxide, potassium t-butoxide and 4-dimethylaminopyridine; salts such as sodium cyanide, potassium cyanide, sodium acetate, potassium acetate, calcium acetate, tin acetate, aluminum acetate, aluminum acetoacetate and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. These catalyst is used singly in combination of two or more.

The amount of the catalyst to be used for the transesterification is preferably 0.001 to 20 mol, more preferably a catalytic amount of 0.01 to 0.05 mol relative to 1 mol of the reactant alcohol compound. The reaction can be carried out without a solvent (the carboxylate ester as the reaction reagent may also serve as the solvent). The solvent-free reaction is preferably because of unnecessity of additional operations such as concentration and solvent recovery. In order to prevent the target compound or a reaction reagent from polymerizing or for other reasons, a solvent can be used supplementarily.

Examples of the solvent to be used for the transesterification include hydrocarbons such as hexane, heptane, benzene, toluene, xylene and cumene; and ethers such as diethyl ether, dibutyl ether, diethylene glycol diethyl ether, diethylene glycol dimethyl ether, tetrahydrofuran and 1,4-dioxane. The solvent can be used singly or in combination of two or more.

The reaction temperature of the transesterification can be selected appropriately in accordance with the type of a carboxylate ester compound to be used and reaction conditions. The reaction is typically carried out with heating. The reaction is preferably carried out at around the boiling point of a lower alcohol having a low boiling point and being generated by the transesterification, while distilling off the generated lower alcohol, so as to obtain better results. The lower alcohol includes methanol, ethanol and 1-propanol, The alcohol may be distilled off under reduced pressure at a temperature lower than the boiling point.

The isolation and purification of the target (2,4,4-trimethyl-1-cyclohexenyl)methyl ester compound (5) can be carried out by a method appropriately selected from purification methods commonly used in organic syntheses, such as vacuum distillation and various types of chromatography. The vacuum distillation is preferable from the standpoint of industrial cost efficiency.

As explained above, the (2,4,4-trimethyl-1-cyclohexenyl) methyl ester compound (5) can be obtained from 2,4,4-trimethyl-2-cyclohexenone (1) in a high yield with high selectivity.

EXAMPLES

The present invention will next be described in further detail with reference to examples. It should not be construed that the present invention is limited to or by them.

Synthesis Example 1

Synthesis of 2,4,4-trimethyl-2-cyclohexenone (1)

The starting material 2,4,4-trimethyl-2-cyclohexenone (1) was synthesized through the following reaction route, specifically by the following method.

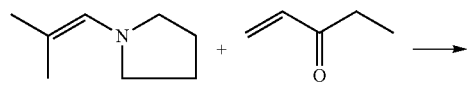

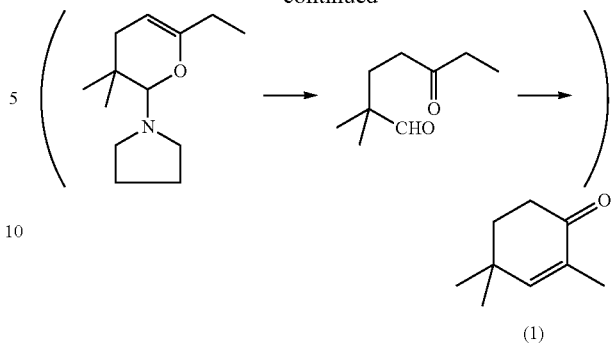

Under a nitrogen atmosphere, 40.4 g of ethyl vinyl ketone was added dropwise to 68.5 g of ice-cooled isobutyraldehyde pyrrolidine enamine over 10 minutes. After the dropwise addition, the temperature of the reaction mixture was gradually increased to room temperature, and the reaction mixture was further stirred at room temperature for 17 hours. The reaction mixture was re-cooled on ice, and then 400 ml of 20% hydrochloric acid was added dropwise thereto. After the dropwise addition, the temperature of the reaction mixture was gradually increased to room temperature, and the reaction mixture was further stirred at room temperature for 30 hours. The reaction mixture was extracted with diethyl ether, then the diethyl ether phase was separated, and the aqueous phase was neutralized with sodium hydrogen carbonate and then was further extracted with diethyl ether. The combined diethyl ether phase was dried over sodium sulfate and concentrated under reduced pressure. The obtained crude product was distilled under reduced pressure to obtain 53.9 g of target compound (yield 82%).

2,4,4-Trimethyl-2-cyclohexenone (1)
Colorless liquid
Boiling point: 76° C./1.9 kPa
IR (D-ATR): ν=2958, 2925, 2867, 1676, 1448, 1362 cm$^{-1}$.
EI-MS (70 eV): m/z=27, 41, 55, 67, 81, 95, 110, 123, 138 (M$^+$).
$^1$H-NMR (500 MHz, CDCl$_3$): δ=1.11 (6H, s), 1.70 (3H, d, J=1.5 Hz), 1.81 (2H, dt-like, J=0.8, 6.9 Hz), 2.42 (2H, t-like, J=7.0 Hz), 6.37-6.39 (1H, m) ppm.
$^{13}$C-NMR (125 MHz, CDCl$_3$): δ=15.91, 27.93 (2C), 32.89, 34.44, 36.33, 132.47, 155.07, 199.73 ppm.

Example 1

Synthesis of (2,4,4-trimethyl-1-cyclohexene)carbaldehyde (3)

Under a nitrogen atmosphere, 13.8 g of 2,4,4-trimethyl-2-cyclohexenone (1) synthesized by the method in Synthesis Example 1 was added dropwise over 30 minutes to an ice-cooled phosphorus ylide solution that had been prepared from 51.4 g of methoxymethyltriphenylphosphonium chloride and 16.8 g of potassium tert-butoxide in a mixed solvent of 245 ml of tetrahydrofuran and 105 ml of toluene. The mixture was stirred for 1 hour still on ice, then stirred overnight at room temperature, and poured into ice water. The organic phase was separated, and the aqueous phase was extracted with diethyl ether. The combined organic phase was washed with a saturated sodium chloride solution, then dried over magnesium sulfate, and concentrated under reduced pressure. N-hexane was added to the residue, and the resulting triphenylphosphine oxide was filtered off. The filtrate was concentrated under reduced pressure, and the obtained crude product was distilled under reduced pressure to obtain 20.43 g of crude 2,4,4-trimethyl-2-cyclohexenylidenemethyl methyl ether. The result of gas chromatographic analysis indicated that the product was a mixture of geometric isomers at 17:83.

A mixture of 18.4 g of the crude product and 100 ml of diethyl ether was subjected to addition of 20 ml of 20% hydrochloric acid, and then stirred at room temperature for 2 hours. The reaction mixture was extracted with n-hexane. The organic phase was washed with a saturated aqueous sodium hydrogen carbonate solution and then with a saturated sodium chloride solution, dried over magnesium sulfate, and concentrated under reduced pressure. The residue was distilled under reduced pressure to obtain 12.6 g of target compound (yield 95%).

The target compound has a gas chromatography purity of 92.2 to 97.8%. Various chromatographic and spectral analyses revealed a trace amount of the isomer, (2,4,4-trimethyl-2-cyclohexene)carbaldehyde, which indicated that the double bond was isomerized from the 2-position to the 1-position, which is the position at which the double bond is conjugated with the carbonyl group of the aldehyde.

(2,4,4-Trimethyl-1-cyclohexene)carbaldehyde (3)
Colorless liquid
Boiling point: 88-91° C./1.06 kPa
EI-MS (70 eV): m/z=29, 41, 56, 67, 81, 95, 109, 123, 137, 152 ($M^+$).
IR (D-ATR): ν=2951, 2922, 2865, 1668, 1636, 1379, 1365, 1247, 754 $cm^{-1}$.
$^1$H-NMR (500 MHz, $CDCl_3$): δ=0.89 (6H, s), 1.35 (2H, t, J=6.5 Hz), 1.97 (2H, br. s), 2.10 (3H, quint-like, J=0.8 Hz), 2.17-2.23 (2H, m), 10.14 (1H, s) ppm.
$^{13}$C-NMR (150 MHz, $CDCl_3$): δ=18.48, 19.98, 28.03 (2C), 28.79, 34.38, 48.13, 132.31, 155.13, 190.84 ppm.

Example 2

To the residue, Synthesis of (2,4,4-trimethyl-1-cyclohexene)methanol (4)

A mixture of 12.67 g of (2,4,4-trimethyl-1-cyclohexene)carbaldehyde (3) synthesized by the method in Example 1 and 50 ml of 95% ethanol was added dropwise to a mixture of 2.50 g of sodium borohydride, 0.1 ml of 25% aqueous sodium hydroxide solution, 25 ml of water and 25 ml of tetrahydrofuran on ice over 10 minutes. The reaction mixture was stirred at room temperature for 1 hour and then was extracted with diethyl ether. The organic phase was washed with a saturated sodium chloride solution, then dried over magnesium sulfate, and concentrated under reduced pressure to obtain 12.79 g of crude product (gas chromatography purity of 95.1%, yield calculated on basis of purity: 98%).

Various chromatographic and spectral analyses of the crude product revealed a trace amount of the isomer (2,4,4-trimethyl-2-cyclohexene)methanol, which indicated that the endocyclic double bond of the cyclohexene ring did not move and the target compound was able to be selectively synthesized. The crude product had sufficient purity as the intermediate and was directly used without purification in the subsequent step.

(2,4,4-Trimethyl-l-cyclohexene)methanol (4)
Colorless liquid
ELMS (70 eV): m/z=29, 41, 55, 69, 79, 93, 107, 121, 139, 154 ($M^+$).
IR (D-ATR): ν=3324, 2949, 2911, 2865, 1450, 1363, 997 $cm^{-1}$.
$^1$H-NMR (500 MHz, $CDCl_3$): δ=0.87 (6H, s), 1.35 (2H, t, J=6.5 Hz), 1.67 (31-1, br.s), 1.73 (3H, br.s), 2.10-2.26 (2H, m), 4.11 (2H, s) ppm.

Example 3

Synthesis of (2,4,4-trimethyl-1-cyclohexenyl)methyl butyrate of Formula (5) in which R is an n-propyl group Under a nitrogen atmosphere, 9.90 g of butyryl chloride was added dropwise over 10 minutes to an ice-cooled mixture of 12.54 g of (2,4,4-trimethyl-1-cyclohexene)methanol (4) synthesized by the method in Example 5, 9.20 g of pyridine, and 150 ml of acetonitrile. The ice bath was removed, and the mixture was stirred at room temperature for 4.5 hours. The reaction mixture was poured into ice water and extracted with n-hexane. The separated organic phase was washed with a saturated aqueous sodium hydrogen carbonate solution and with a saturated sodium chloride solution, then dried over magnesium sulfate, and concentrated under reduced pressure.

The obtained residue was distilled under reduced pressure to obtain 14.86 g of target compound (yield 86%).

(2,4,4-trimethyl-1-cyclohexenyl)methyl butyrate
Colorless liquid
Boiling point: 72-74° C./530 Pa
EI-MS (70 eV): m/z=27, 43, 55, 79, 93, 107, 121, 136, 224 ($M^+$).
IR (D-ATR): ν=2951, 2912, 2875, 1734, 1455, 1364, 1174 $cm^{-1}$.
$^1$H-NMR (500 MHz, $CDCl_3$): δ=0.87 (6H, s), 0.94 (3H, t, J=7.3 Hz), 1.34 (2H, t, J=6.5 Hz), 1.61-1.69 (5H, m), 1.76 (2H, br.s), 2.01-2.06 (2H, m), 2.28 (2H, t-like, J=7.2 Hz), 4.58 (2H, s) ppm.
$^{13}$C-NMR (150 MHz, $CDCl_3$): δ=13.65, 18.52, 19.24, 25.54, 28.12 (2C), 28.97, 35.43, 36.26, 45.97, 64.33, 123.70, 132.15, 173.94 ppm.

The invention claimed is:
1. A method for producing (2,4,4-trimethyl-1-cyclohexene)carbaldehyde, comprising the steps of:
reacting a carbonyl group of 2,4,4-trimethyl-2-cyclohexenone of Formula (1):

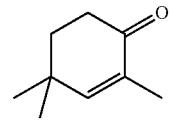

(1)

with a triphenylphosphonium alkoxymethylide of formula $(C_6H_5)_3P=CHOR^1$, wherein $R^1$ is a monovalent hydrocarbon group having 1 to 8 carbon atoms, to obtain a 2,4,4-trimethyl-2-cyclohexenylidenemethyl ether compound of General Formula (2):

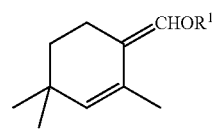

(2)

wherein $R^1$ is as recited above; and hydrolyzing the 2,4,4-trimethyl-2-cyclohexenylidenemethyl ether to obtain the (2,4,4-trimethyl-1-cyclohexene)carbaldehyde of Formula (3):

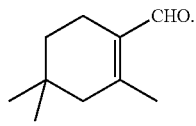
(3)

2. A method for producing (2,4,4-trimethyl-1-cyclohexene)methanol, comprising:
the steps comprised by the method according to claim 1 to obtain the (2,4,4-trimethyl-1-cyclohexene)carbaldehyde; and
a step of reducing the (2,4,4-trimethyl-1-cyclohexene)carbaldehyde to obtain the (2,4,4-trimethyl-1-cyclohexene)methanol of Formula (4):

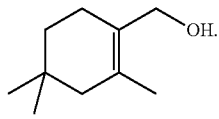
(4)

3. A method for producing a (2,4,4-trimethyl-1-cyclohexenyl)methyl ester compound, comprising:
the steps comprised by the method according to claim 2 to obtain the (2,4,4-trimethyl-1-cyclohexene)methanol; and
a step of esterifying the (2,4,4-trimethyl-1-cyclohexene)methanol with a compound selected from the group consisting of an acylating agent, a carboxylic acid, and a carboxylic ester to obtain the (2,4,4-trimethyl-1-cyclohexenyl)methyl ester compound represented byof General Formula (5):

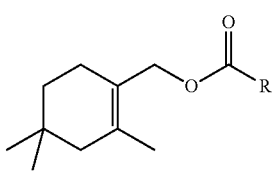
(5)

wherein R is a hydrogen atom or a monovalent hydrocarbon group having 1 to 10 carbon atoms.

* * * * *

UNITED STATES PATENT AND TRADEMARK OFFICE
CERTIFICATE OF CORRECTION

PATENT NO. : 9,708,241 B2
APPLICATION NO. : 15/021168
DATED : July 18, 2017
INVENTOR(S) : Kinsho et al.

It is certified that error appears in the above-identified patent and that said Letters Patent is hereby corrected as shown below:

On the Title Page

Item (56) References Cited, Other Publications, Page 2: Please correct "*Hydroboration, 4th edition* pp 72-81." to read -- *Hydroboration, 4th edition* pp 72-81. (1992) --

In the Specification

Column 2, Line 49: Please correct "Red. Tray. Chim." to read -- Recl. Tray. Chim. --

Column 4, Lines 27-28: Please correct "(2,4,4-trimethyl-1-cyclohexenyemethyl" to read -- (2,4,4-trimethyl-1-cyclohexenyl)methyl --

Column 13, Line 64: Please correct "ELMS" to read -- EI-MS --

Column 14, Line 2: Please correct "(31-1, br.s)" to read -- (3H, br.s) --

In the Claims

Column 16, Claim 3, Line 11: Please correct "compound represented byof" to read -- compound of --

Signed and Sealed this
Nineteenth Day of June, 2018

Andrei Iancu
*Director of the United States Patent and Trademark Office*